United States Patent [19]

Eberwine

[11] Patent Number: 6,020,136
[45] Date of Patent: Feb. 1, 2000

[54] IDENTIFICATION OF FUNCTIONAL TRANSCRIPTION FACTORS SYNTHESIZED IN DEVELOPING NEURONS

[75] Inventor: James Eberwine, Philadelphia, Pa.

[73] Assignee: The Trustees of the University of Pennsylvania, Philadelphia, Pa.

[21] Appl. No.: 09/154,477

[22] Filed: Sep. 16, 1998

Related U.S. Application Data

[60] Provisional application No. 60/059,227, Sep. 18, 1997.

[51] Int. Cl.[7] ................................................ C12Q 1/68
[52] U.S. Cl. ...................................................... 435/6
[58] Field of Search ..................................... 435/6

[56] References Cited

PUBLICATIONS

Black et al., "Effects of Surgical Decentralization and Nerve Growth Factor on the Maturation of Adrenergic Neurons in a Mouse Sympathetic Ganglion", (1972) *J. Neurochem.* 19:1367–1370.

Crino and Eberwine, "Molecular Characterization of the Dendritic Growth Cone: Regulated mRNA Transport and Local Protein Synthesis", (1996) *Neuron* 17: 1173–87.

Davis et al., "Selective dendritic transport of RNA in hippocampal neurons in culture", (1987) *Nature* 330:477–479.

Eberwine et al., "Analysis of gene expression in single live neurons", (1992) *Proc. Natl. Acad. Sci.* 89:3010–3014.

Garner et al. "Familial predisposition to Wilms' tumor does not map to the short arm of chromosome 11", (1988) *Nature* 336:374–377.

Ghosh et al., "Requirement for BDNF in Activity–Dependent Survival of Cortical Neurons", (1994) *Science* 263:1618–1623.

Goodman and Schatz, "Development Mechanisms That Generate Precise Patterns of Neuronal Connectivity", (1993) *Cell/Neuron* 72/10 (S):77–98.

Kater and Mills, "Regulation of Growth Cone Behavior by Calcium", (1991) *J. Neurosci.* 11:891–899.

Lankford et al., "Nerve growth cone motility", (1990) *Curr. Opinion Cell Biol.* 2:80–85.

Lee, "Basic helix–loop genes in neural development", (1997) *Curr Opin Neurobiol.* 7:13–20.

Lyford et al., "Arc, a Growth Factor and Activity–Regulated Gene, Encodes a Novel Cytoskeleton–Associated Protein That Is Enriched in Neuronal Dendrites", (1995) *Neuron* 14:433–445.

Miyashiro et al., "On the nature and differential distribution of mRNAs in hippocampal neurites: Implications for neuronal functioning", (1994) *Proc. Natl. Acad. Sci.* 91: 10800–10804.

Paldino and Purpura, "Branching Patterns of Hippocampal Neurons of Human Fetus during Dendritic Differentiation", (1979) *Exp. Neurol.* 64: 620–631.

Steward, "Preferential Localization of Polyribosomes Under the Base of Dendritic Spines in Granule Cells of the Dentate Gyrus[1]", (1982) *J. Neurosci.* 2:284–291.

Steward et al., "Protein Synthesis and Processing in Cytoplasmic Microdomains Beneath Postsynaptic Sites on CNS Neurons", (1992) *Mol. Neurobiol.* 2:227–261.

Tanaka and Sabry, "Making the Connection: Cytoskeletal Rearrangments during Growth Cone Guidance", (1995) *Cell* 83:171–176.

Waeber and Habener, "Nuclear Translocation and DNA Recognition Signals Colocalized within the bZIP Domain of Cyclic Adenosine 3',5'–Monophosphate Response Element-–Binding Protein CREB", (1991) *J. Mol. Endo* 5:1431–1438.

*Primary Examiner*—Terry McKelvey
*Attorney, Agent, or Firm*—Law Offices of Jane Massey Licata

[57] ABSTRACT

The present invention relates to the identification of biologically active transcription factors which are synthesized and modified in the dendritic compartment of neurons and uses thereof.

1 Claim, No Drawings

6,020,136

IDENTIFICATION OF FUNCTIONAL TRANSCRIPTION FACTORS SYNTHESIZED IN DEVELOPING NEURONS

This application claims the benefit of U.S. Provisional Application No. 60/059,227, filed Sep. 18, 1997. +gi

INTRODUCTION

This invention was made in the course of research sponsored by the National Institutes of Health. The U.S. Government may have certain rights in this invention.

BACKGROUND OF THE INVENTION

The organization of connections made in the central nervous system is determined by the turnover of particular cell types in conjunction with the axonal and dendritic growth of individual neurons (Paldino and Purpura (1979) *Exp. Neurol.* 64: 620–631; Black et al. (1972) *J. Neurochem.* 19:1367–1370). These developing neurons express thousands upon thousands of membrane specializations at synaptic contact sites on their dendrites which become more elaborate as they age. This development process is referred to as arborization. Arborization begins after neurons have migrated to their appropriate cortical layer and continues throughout the life of the cell. It is believed that the purpose of these arborizations is to make the suitable synaptic connections at any given time (Lankford et al. (1990) *Curr. Opinion Cell Biol.* 2:80–85, Tanaka and Sabry (1995) Cell 83:171–176).

The construction and maintenance of these membrane specializations, referred to as "growth cones", which protrude from the distal tips of dendrites are influenced by a variety of factors. For example, it has been shown that extension, collapse, and directional turning in vitro can be altered by a change in Ca++ influx as well as the presence of extracellular matrix molecules (Goodman and Schatz (1993) *Cell/Neuron* 72/10 (S):77–98; Kater and Mills (1991) *J. Neurosci.* 11:891–899). In addition, multiple proteins important for dendritic outgrowth have been identified. The majority of these are translated elsewhere and transported to the dendrite and growth cones. However, some of the necessary proteins are believed to be synthesized locally. For example, mRNAs for microtubule associate protein 2 (MAP2), the alpha subunit of Ca++/calmodulin-dependent protein kinase II, brain-derived neurotrophic factor (BDNF), activity-regulated cytoskeleton associated protein (ARC), and several glutamate receptor subtypes have all been identified within dendrites or growth cones (Garner et al. (1988) *Nature* 336:374–377; Miyashiro et al. (1994) *Proc. Natl. Acad. Sci.* 91: 10800–10804; Ghosh et al. (1994) *Science* 263:1618–1623; and Lyford et al. (1995) *Neuron* 14:433–445). In addition, ultrastructural studies have shown the preferential localization of polyribosomes beneath postsynaptic sites and occasionally associated with membrane specializations on dendrites (Steward (1982) *J. Neurosci.* 2:284–291, Steward et al. (1992) *Mol. Neurobiol.* 2:227–261). Thus, local translation of growth cone mRNAs may provide a novel mechanism by which proteins necessary for changes in growth cone morphology may be synthesized within growth cone cytoplasm during dendritic arborization (Davis et al. (1987) *Nature* 330:477–479).

More recently, it has been shown that mRNAs may be locally translated into proteins in individual dendrites and dendritic growth cones (Crino and Eberwine (1996) *Neuron* 17: 1173–87). Using a differential display expression analysis in individually dissected growth cones, it was shown that certain mRNAs within these processes became increasingly more complex at each stage of dendritic outgrowth. For example, BDNF, MAP2, and the GABA-A receptor subunit, Ca-N transcripts increased in abundance in growth cones up to 72 hours in culture. Many of the mRNAs that are present in growth cones at 72 hours in culture have been identified in mature dendrites, suggesting that these mRNAs may be important for synaptogenesis, maintenance of fully arborized mature dendrites, and synaptic plasticity as well as the functional transition from pathfinding to specialization into postsynaptic terminals. In addition, mRNA transfected into dendrites and manually separated from their cell body was found to be translated into immunohistochemically detectable protein. Thus, protein synthesis is possible within restricted subcellular domains such as dendrites and growth cones.

Specific transcription factor mRNAs localized in dendrites and dendritic growth cones have now been identified. Further, these dendritically synthesized transcription factors have been demonstrated to modulate nuclear gene transcription in response to trophic or other cues. This process, termed "nuclear imprinting" permits signals acting on distal tips of growing dendrites to have a direct impact on gene transcription rather than via the integrated response of signal transduction cascade mechanisms which converge on the nucleus to alter the functioning of nuclear localized transcription factors. It has further been shown that this process of nuclear imprinting depends on the determination of the functional ability and activation state of the dendritically synthesized transcription factor.

SUMMARY OF THE INVENTION

An object of the present invention is to methods of identifying functional dendritic transcription factors which comprise isolating mRNAs of dendritic growth cones; preparing cDNAs from the isolated mRNAs; screening the cDNAs to detect transcription factor mRNAs; and determining whether the transcription factor is activated and thus functional in the dendrite.

Another object of the present invention is to provide isolated dendritic transcription factors identified by these methods.

Yet another object of the present invention is to provide methods of identifying agents which modulate neural gene transcription by identifying functional dendritic transcription factors; contacting dendrites with an agent suspected of modulating activation of the identified dendritic transcription factor; and determining whether the agent modulates activation of the identified dendritic transcription factor.

DETAILED DESCRIPTION OF THE INVENTION

The growth and development of a neural network is, in part, regulated by the elaboration of dendritic arbors from neurons that results in the appropriate synaptic connection. These processes are dynamic entities which extend, collapse, and turn in response to a variety of signals, such as Ca++ influx. While many of the proteins important for dendritic outgrowth are transported to dendrites and growth cones, several proteins essential for this process appear to be locally synthesized. For example, structural proteins such as MAP2 or ARC, or signal transduction molecules like CaM kinase II have been found to be synthesized locally. In addition, select transcription factors, such as zif268, have now been identified as being among the mRNA specifically found in dendrites. These dendritically synthesized transcription factors, in response to trophic or other cues, are believed to modulate nuclear gene transcription thereby bypassing signal transduction cascade mechanisms.

To identify these dendritically synthesized transcription factors, primary dissociated neuronal cultures were generated from embryonic rat hippocampi at day 18. Dendrites (from 48 and 72 hour cultures) were distinguished from axons on the basis of tapering caliber, nascent branch pattern, immunoreactivity for MAP2 and absence of GAP 43 antigenicity. In addition, growth cones were visually identified using phase contrast microscopy on the distal aspects of the tips of dendrites. Individual dendritic growth cones were transected at the point of attachment using glass recording microelectrodes filled with reagents necessary for cDNA synthesis (Miyashiro et al. (1994) Proc. Natl. Acad. Sci. 91: 10800–10804; Crino and Eberwine (1996) Neuron 17: 1173–87). After transection, growth cones were gently aspirated into the electrodes and cDNA synthesis was performed by methods known to those of skill in the art. Cell bodies from which growth cones were harvested were also aspirated for comparison and amplified antisense RNA (aRNA) synthesis was performed (Eberwine et al. (1992) Proc. Natl. Acad. Sci. 89:3010–3014).

Transcription factor cDNAs prepared from the RNAs were screened utilizing $^{32}$P-CTP radiolabeled aRNA in reverse Northern blots. Examples of transcription factors which play important roles during neuronal development and which may be synthesized locally include, but are not limited to; the δ isoform of CREB (cAMP response element binding protein), c-fos, c-jun, zif268, OTX-1, BF-1/BF-2, and HES-1. The α subunit of Ca2+/calmodulin dependent kinase (CamKII) and microtubule associated protein 2 (MAP2) cDNAs, which have been previously identified in dendrites serve as positive controls for the appropriate amplification of growth cone mRNAs.

Using this method, CREB and zif 268 mRNAs were detected whereas c-fos, c-jun, OTX-1, HES1, BF-1 and BF-2 mRNAs were not detected in dendritic growth cones. However, all of these transcription factor mRNAs were detected in the cognate neuronal cell bodies.

Thus, to gain a broader view of transcription factor mRNAs in the dendritic domain, arrayed blots of several hundred —$C_2H_2$ zinc finger containing cDNAs were probed with radiolabeled aRNA from cell bodies or growth cones. Hybridization to several —$C_2H_2$ cDNAs probed with cell body aRNA (>15 positives) and growth cone aRNA (5 positives) were observed. The finding of only a few —$C_2H_2$ transcription factor mRNAs and the original reverse northern analysis in dendrites highlights the selectivity of transcription factor mRNA localization in growth cones. Because of CREB's suggested role in neuronal plasticity, the dendritic localization was confirmed by PCR, DNA sequencing of the PCR product and in situ hybridization. The evolutionary conservation of CREB mRNA localization to dendrites in intact tissue was confirmed by the in situ hybridization detection of CREB mRNA in pyramidal cell dendrites of human brain sections.

Activation of the transcription factor within the dendrite was then confirmed.

In one embodiment, cultured hippocampal neurons were stained with polyclonal antibodies by methods known to those of skill in the art which recognize either non- or phosphorylated CREB (Ab244), the leucine zipper domain of CREB (ZE244), or Ser$^{133}$ phosphorylated CREB. Dense Ab244 and ZE244 immunoreactivity was observed within the nucleus, while lighter staining were observed in the somatic, dendritic, and dendritic growth cone cytoplasm. Growth cones with broadened lamellopodia were most intensely stained, while many smaller growth cones were not labeled or lightly labeled. In addition, CREB immunoreactivity in morphologically characterized axons was not observed. Immunoabsorption of Ab244 antibodies with CREB peptide substantially diminished immunolabeling in both nuclei and dendrites and demonstrated that antibody staining is specific for CREB. Ser$^{133}$ phosphorylated CREB staining was noted in dendrites and growth cones after treatment with either BDNF or NT3 (100 ng/ml), but not with KCl (60 μM), suggesting that specific factors can induce phosphorylation of CREB in the dendroplasm. The phosphorylation state of Ser$^{133}$ in CREB is an important switch in regulating CREB transcriptional activity since CREB mediated transcription is activated when Ser$^{133}$ is phosphorylated. Further evidence of selective CREB regulation in the dendrite was provided by the lack of phospho-CREB immunoreactivity in the axon.

An in situ southwestern assay (ISSW) was then employed to assess whether the CRE octanucleotide recognized by CREB could bind to the DNA binding domain/leucine zipper region of CREB. The palindromic CRE oligonucleotide (TGACGTCA)(SEQ ID NO: 1) was radiolabeled with $^{32}$P-γATP to high specific activity (>$10^9$ cpm/mg) and then ligated with unlabeled CRE oligomers to yield a pool of $^{32}$P-labeled CRE concatamers varying in size up to several hundred basepairs in length. The radiolabeled CRE concatamers were incubated for 2–3 hours at room temperature with cultured E18 hippocampal neurons which had been fixed for 5 minutes in 4% paraformaldehyde. Photoemulsion dipped slides are viewed under darkfield optics. The CRE concatamers bound to CREB protein in the nuclei, dendrites, and dendritic growth cones within neurons and corroborated the immunohistochemical identification of CREB in these domains. Highly concentrated grain density is observed within the nucleus whereas more punctate labeling is present within dendrites and dendritic growth cones. Axons did not exhibit CREB binding of the CRE concatamer. Unligated radiolabeled $^{32}$P-CRE oligonucleotide did not bind to protein in the cells. Moreover, pre-incubation of the tissue section with a high molar excess (>5 mg) of non-radiolabeled ligated CRE served to effectively compete with labeled concatamer to abolish $^{32}$P-CRE concatamer binding to CREB. Finally, no binding was detected with a nonsense palindrome probe (inverted CRE sequence, 5'-CAGTACTG-3') (SEQ ID NO: 2) which was used to assess whether binding of the CRE concatamer reflected a non-specific interaction of double stranded DNA with other transcription factor proteins.

To demonstrate that CREB mRNA is recognized by the translational machinery present in dendroplasm, a myc-tagged CREB mRNA was transfected into isolated dendrites (cell bodies removed) using DOSPER lipid mediated transfection (Boehringer Mannheim, Indianapolis, Ind.). Following application of the lipid:mRNA, dendrites were treated with BDNF or NT3 (100–200 ng/ml) to stimulate protein synthesis. The translated fusion protein is visualized in transected dendrites and growth cones using anti-myc antibodies. Control transfections with buffered saline, pGEM plasmid mRNA:lipid, or lipid:tRNA complexes were negative for myc-staining. Indeed, immunoreactive myc-tagged CREB was not detected without application of BDNF or NT3 suggesting that effects of these compounds in vivo are important in modulating dendritic CREB protein synthesis locally in individual isolated dendrites and growth cones. Additional agents which modulate dendritic transcription factors can also be determined by this method.

To assess the possibility of anterograde or retrograde transport of dendritic CREB protein, CREB protein was tagged with the fluorescent marker Oregon Green (Molecular Probes, Eugene, Oreg.) through linkage of succinimyl-groups of the fluorochrome to lysines in the CREB protein (ogCREB). Oregon Green labeled bovine serum albumin (ogBSA) serves as a diffusion and nonspecific protein control. ogCREB or ogBSA were microperfused into the cell body or distal dendrite via recording electrode under whole cell patch clamp conditions. OgBSA introduced into the soma or dendrites of neurons diffused rapidly throughout the cell. ogCREB introduced into the cell soma did not diffuse into the dendrite or axons and concentrated in the nucleus. When ogCREB was perfused into dendrites, it moved unidirectionally from the dendrite into the cell soma and became concentrated in the nucleus. This indicates that dendritic CREB protein is synthesized locally from dendritic CREB mRNA and that the translocation machinery necessary to transport CREB to the nucleus is present within the dendritic domain. Thus, CREB protein present in dendrites is capable of exerting a direct action upon gene expression by its select and rapid transport to the nucleus likely via interaction of its endogenous nuclear localization signal with the translocation machinery (Waeber and Habener (1991) *J. Mol Endo* 5:1431–1438).

Many transcription factors such as CREB, regulate gene expression in response to membrane depolarization, $Ca^{++}$ influx, and cAMP-mediated second messenger systems. CREB phosphorylation is tightly coupled to synaptic plasticity, long term potentiation, and genesis of dendritic spines suggesting that cellular events occurring at a distance from the nucleus are closely linked to the activation state of CREB within the nucleus (Lee (1997) *Curr Opin Neurobiol.* 7:13–20). Detection of phospho-$Ser^{133}$ CREB in dendrites after neurotrophic factor treatment provides a compelling example of how specific stimuli can induce the formation of activated CREB.

The identification of transcription factors which are synthesized distal from their putative site of action, where post-translational modifications (e.g. phosphorylation) are regulated in the nucleus provides a mechanism through which local pharmacologic (such as neurotrophic factors) and electrophysiologic signals at the synapse can effect specific changes in neuronal gene transcription. For example, the formation of functional CREB dimers which strongly interact with the CRE site is dependent on phosphorylation by PKC and other kinases such as CamKII, CamKIV, and PKA. While there is little CamKII in neuronal nuclei, it is enriched in dendrites. Since CREB protein has a consensus site $Ser^{133}$ for CamKII phosphorylation, CamKII (activated by Ca++ influx into the cell) may phosphorylate dendritic but not nuclear CREB. The phosphorylation state of CREB and other transcription factors specifically synthesized and modified in the dendritic compartment, where kinases and phosphatases are distinct from those in the nucleus, may account for aspects of spatial regulation of gene expression through $Ca^{2+}$ mediated mechanisms. Upon identification of functional dendritic transcription factors using the method of the present invention, one of skill in the art can routinely screen for agents which alter activation of the transcription factors thereby modulating neuronal gene transcription. Transcription factors have also been shown under certain conditions to act as RNA binding proteins. Such RNA binding proteins are believed to be important in mRNA transport and/or regulation of protein synthesis. Accordingly, agents identified as targeting and modulating activation of functional dendritic transcription factors may be useful in regenerating activity and function of severed dendrites, for example, in spinal cord injuries.

The following nonlimiting examples are provided to further illustrate the present invention.

EXAMPLES

Example 1
Immunohistochemistry of Neurons

Hippocampal neurons were immunolabeled with rabbit polyclonal antibodies to non-phosphorylated CREB, $Ser^{133}$ phosphoCREB (Ab244), or the leucine zipper containing region of CREB (ZE244) in 0.1 M TRIS/5% horse serum overnight at 4° C. Antibody labeling was performed via the avidin-biotin method (ABC Vectastain, Vector Laboratories, Burlingame, Calif.) and visualized with 3,3'-diaminobenzidine (DAB).

Example 2
aRNA Analysis of Dendritic mRNA

Growth cones were transected at the basal point of attachment to the dendrite using recording microelectrodes filled with reagents necessary for single cell mRNA amplification. Reagents include electrode buffer (HEPES buffer 10 mM (pH 7.4), $MgCl_2$ 1 mM, KCl 120 mM), oligo-dT-T7 probe, diethyl pyrocarbonate (DEPC) treated $H_2O$, and avian myeloblastosis reverse transcriptase (0.5 U/µl). After transfection, growth cones were gently aspirated into the electrodes and cDNA synthesis was performed for 90 minutes at 40° C. Double-stranded template cDNA synthesis was with T4 DNA polymerase I (Boehringer-Mannheim, Indianapolis, Ind.). cDNA was amplified (aRNA) with T7 RNA polymerase incorporating $^{32}P$-CTP as a radiolabel. A second round of DNA synthesis was performed followed by a second aRNA amplification incorporating $^{32}P$-CTP. Radiolabeled aRNA was used as a probe for reverse Northern (slot) blot analysis.

Example 3
In situ Southwestern Assay

The CRE octamer (5'-TGACGTCA-3' (SEQ ID NO: 1); 100 ng) was radiolabeled with T4 polynucleotide kinase and $^{32}P$-γATP. The radiolabeled octamer was then ligated with 1 mg unlabeled oligonucleotide. Hippocampal neurons which were fixed in 4% paraformaldehyde were incubated in 0.1 M TRIS/0.1% Triton-X followed by incubation o/n at RT in DNA binding buffer (250 mM HEPES buffer (pH 7.4), 5×Denhardt's solution, sheared single stranded salmon sperm DNA (200 mg/ml), 0.01 mM $MgCl_2$, and 0.03 mM KCl). The various probes were added to fresh binding buffer, and applied to cells for 4 hours at room temperature. For competition experiments, 5 mg unlabeled ligated CRE concatamer was preincubated with the cells for 4 hours prior to addition of the CRE probe. Cells were then washed in binding buffer. The coverslips were dipped in Kodak NT2 photographic emulsion and exposed for 72 hours at 4° C. Slides were developed in Kodak D19 developer at 14° C., rinsed in $dH_2O$, and viewed under darkfield microscopy.

Example 4
Single Dendrite Transfection

Capped CREB-myc mRNA was synthesized in vitro using the Ambion Megascript kit. The CREB-myc mRNA was complexed with the cationic lipid DOSPER (Boehringer-Mannheim) and carrier tRNA (5 µg) in HEPES buffered saline (20 mM HEPES, 150 mM NaCl) at room temperature for 20 minutes prior to use. Methods of removal of the cell soma, dendritic transfection and myc-immunohistochemistry are well known to those of skill in the art.

Example 5
Fluorescent Tagging and Microperfusion of Protein

CREB protein (10 mg) was mixed with 10 ml of 0.2 M sodium bicarbonate (pH 8.3). Two microliters of Oregon Green 514 carboxylic acid, succinimidyl ester (10 mg/ml in DMSO; #06139, Molecular Probes, Eugene Oreg.) was added and the mixture stirred for 60 minutes at room temperature. Two milliliters of freshly prepared 1.5 M hydroxylamine (pH 8.5) was added and the solution incubated for 30 minutes. To this mixture was added 10 ml of a non-specific peptide bound to silica beads which was incubated at room temperature for an additional 30 minutes. After centrifugation at 12,000 g for 30 seconds the liquid phase was transferred to another tube. This liquid phase was drop dialyzed at room temperature in the dark for 2 hours against 1×intracellular patch pipette solution (145 mM K gluconate, 8 mM KCl, 10 mM K-HEPES 3 mM MgATP, pH 7.2, osmolality of 287 mosmol/kg).

Hippocampal neurons were visualized with a Zeiss Axioskop using a 63×, 0.9 NA water immersion infinity-corrected objective. Cells were voltage clamped employing the whole-cell patch clamp technique by patching on the soma (1.2–3 Mohms) or the dendrites (12–18 Mohms). The extracellular solution (150 mM NaCl, 2.5 mM $CaCl_2$, 1.5 mM $MgCl_2$ and 10 mM Na-HEPES, pH 7.4, osmolality of 295 mosmol/kg) was supplemented with free fluorophore (Oregon Green 514) and ogCREB or ogBSA. Promptly after establishing the whole-cell recording the free fluorophore diffused from the patch pipette into the cytosol and equilibrated (~2 minutes). An initial image of the fluorescence emitted from the cell was taken at this time using a CCD imaging camera (1 or 5 second exposures; EEV chip) employing epifluorescence microscopy with 485 and 530 nm DF band pass excitation and emission filters (full half width maximums of 22 and 30 nm respectively), and a 505 nm long pass 45° dichroic filter. Subsequent images were taken up to 70 minutes after the initial image as long as the holding current was less than −100 pA at a holding potential of −60 mV. ΔF/F images were calculated after correcting for background fluorescence, by subtracting the initial image from the images taken at later times, and then dividing the resulting image by the initial image. The ΔF/F images, therefore, provide a measure of the slower diffusion/transport of the fluorescently tagged proteins and are independent of variables such as differences in the optical pathlength and nonuniformity of incident light.

What is claimed is:
1. A method of identifying functional dendritic transcription factors comprising:
   (a) isolating mRNAs of dendritic growth cones;
   (b) preparing cDNAs from the isolated mRNAs;
   (c) screening the cDNAs to detect the cDNAs which encode a transcription factor; and
   (d) determining whether the transcription factor is functional in the dendrite.

* * * * *

SEQUENCE LISTING

```
<160> NUMBER OF SEQ ID NOS: 2

<210> SEQ ID NO 1
<211> LENGTH: 8
<212> TYPE: DNA
<213> ORGANISM: Rattus sp.

<400> SEQUENCE: 1 tgacgtca                                                         8

<210> SEQ ID NO 2
<211> LENGTH: 8
<212> TYPE: DNA
<213> ORGANISM: Rattus sp.

<400> SEQUENCE: 2 cagtactg                                                         8
```